United States Patent [19]

Rosen et al.

[11] Patent Number: 5,034,221

[45] Date of Patent: Jul. 23, 1991

[54] TOPICAL AGENT AND METHOD FOR THE TREATMENT OF PSEUDOFOLLICULITIS BARBAE

[76] Inventors: Steven E. Rosen, 2150 SW. 90th Ave., #A, Ft. Landerdale, Fla. 33324; Robert M. Thomas, 2052 Cottage St., Ft. Myers, Fla. 33901

[21] Appl. No.: 369,938

[22] Filed: Jun. 22, 1989

[51] Int. Cl.$^5$ ................................................ A61K 7/15
[52] U.S. Cl. ...................................... 424/73; 514/589; 514/164; 514/171; 514/21; 514/848; 514/859; 514/880; 514/159; 514/165
[58] Field of Search .................. 424/73; 514/589, 164, 514/171, 21, 848, 859, 880, 159, 165

[56] References Cited

U.S. PATENT DOCUMENTS

| | | | |
|---|---|---|---|
| 3,530,217 | 9/1970 | White | 424/180 |
| 4,219,548 | 8/1980 | Reller | 424/234 |
| 4,369,180 | 1/1983 | Mihalovits | 424/195 |

*Primary Examiner*—Thurman Page
*Assistant Examiner*—D. Gabrielle Phelan
*Attorney, Agent, or Firm*—Melvin K. Silverman

[57] ABSTRACT

A topical agent and method for the treatment and prevention of pseudofolliculitis barbae, commonly known as "razor bumps", is effected by the topical application to beard areas of the face of a combination of acetylsalicylic acid, corn starch, isopropyl alcohol, and aloe vera.

12 Claims, No Drawings

TOPICAL AGENT AND METHOD FOR THE TREATMENT OF PSEUDOFOLLICULITIS BARBAE

BACKGROUND OF THE INVENTION

The present invention relates to a disorder known as pseudofolliculitis barbae and, more particularly, to a product in the nature of a topical preparation and a method for the treatment and prevention of psuedofolliculitis barbae.

Pseudofolliculitis barbae is the clinical name given to the condition commonly known as "razor bumps". Generally, this condition describes the ingrowth of emerged facial hairs back into the skin at a location currently adjacent to the follicle from which the hair has emerged. This penetration back into the skin causes an antigenic foreign body reaction at the point of re-penetration, resulting in lesions consisting of firm papules and pustules in which the ingrown hair can become buried. Further, infections can become super imposed upon this basic state, augmenting the inflammatory reaction. Resultingly, further shaving becomes difficult and painful.

From the point of view of physiomechanics, pseudofolliculitis barbae is caused by strongly curved facial hairs. For this reason, the condition tends to have a greater incidence in males of the Negro race. These curved facial hairs emerge closely parallel to the skin and, owing to their curvature, are mechanically biased toward re-entry into the skin. Because of their initial emergence so close to the skin surface, these hairs often are not closely cut, at their point of emergence during shaving. In practice, shaving operates to aggravate the condition because shaving serves to obliquely cut the biased hair, above the skin surface, leaving a relatively sharp point at the tips which facilitates skin penetration. As such, the act of shaving is at least a partial cause of the condition itself.

Between one shave and the next, the point or tip of the skin ingrows into the skin, bringing about the reaction and conditions set forth above.

Those suggestions which exist for dealing with the condition of psuedofolliculitis barbae involve both treatment and prevention. In terms of treatment, it is necessary to bathe any lesions and associated secondary infections, and for this reason various therapeutic agents and antibiotics have been suggested. The effects of the condition can then be held in check. Abstinence from shaving is generally then necessary because continued growth of the curved facial hair will eventually result in a spring-like action which will pull the ingrown tip out of the skin.

However, as may be appreciated, total abstinence from shaving is not, for the most part a practical solution to the problem.

Prevention of pseudofolliculitis barbae has proven difficult. In theory, frequent shaving which cuts emerging facial hairs exactly at the skin surface would eliminate the condition by regularly removing the hairs before they have an opportunity to grow and re-enter the skin. The difficulty therein is that cutting of facial hairs precisely at skin level is difficult and frequent shaving will bring with it the condition of sharp hair ends which might actually hasten the onset of the condition. Some efforts to cut facial hair at the skin level have involved the stretching of the skin, which actually results in the cutting of the hairs below the skin level. This can result in an intra-follicular ingrown hair in which the sharp tip curved hair, instead of emerging from the follicle, penetrates the follicular wall and bring about the same or similar foreign body reaction as would occur when a hair normally emerges from the follicle but then re-enters the skin.

The use of depilatory compositions has been suggested for the prevention of pseudofolliculitis barbae. For some, this can be effective in achieving the non-cutting removal of the hairs before they can re-enter the skin. However, for others, the depilatory itself can become an irritant.

Also suggested have been compositions which soften the facial hair to inhibit their inability to penetrate the skin. However, most of these compositions bring about skin irritations or other dermatologist side effects when used with a frequency required to ensure prevention of the condition.

Prior art known to the inventors concerning the subject of pseudofolliculitis barbae includes U.S. Pat. Nos. 3,981,681; 4,228,163; 4,525,344; and 4,775,530. None of these references teach or suggest a topical solution of the combination of acetylsalicylic acid, corn starch, isopropyl alcohol and aloe vera.

Also known to the inventors herein is U.S. Pat. No. 4,219,548 (1980) to Reller, entitled Topical Anti-Inflammatory Composition; U.S. Pat. No. 4,364,940 (1982) to Neiss, entitled Compositions for Treating Acne; and U.S. Pat. No. 4,665,063 (1987) to Bar-Shalom, entitled Method of Treating Acne. Each of these references deal with the use, in one form or another, of acetylsalicylic acid; however, therein, the dermatological condition of concern is that of acne. Acne, may be appreciated, differs materially from pseudofolliculitis barbae. More particularly, acne is an inflammatory process involving the sebaceous or oil glands of the skin and, most notably, the skin of the face. Whereas pseudofolliculitis barbae has nothing to do with the sebaceous glands. Rather, pseudofolliculitis barbae results from, as has been noted above, the ingrowth of emerged facial hair back into the skin, adjacent to the follicle from which the hair has emerged. Accordingly, the respective uses which have been, in the prior art of acetylsalicylic acid, suggested with respect to the treatment of acne, are not applicable to the use of acetylsalicylic acid in the invention set forth herewith.

While said U.S. Pat. No. 4,665,063 to Bar-Sholom employs, in one modification (Example VII) of its disclosed formula, a combination of acetylsalicylic acid and isopropyl alcohol, this combination is used by Bar-Sholom to treat psoriasis and seborrhea. These dermatologic disorders are totally unrelated to pseudofolliculitis barbae and, in particular, seborrhea and psoriasis, both are characterized by crusting and flaking lesions of the skin, which symptoms do not occur in pseudofolliculitis barbae. Also the condition of seborrhea and psoriasis are not limited to the facial skin as is the case in pseudofolliculitis. Further, while the mechanism of action of psuedofolliculitis is known, the cause of seborrhea and psoriasis remain unknown.

In addition to the Example No. VII of Bar-Sholom, that being the combination of acetylsalicylic acid and isopropyl alcohol, the instant inventive preparation requires two further ingredients to function within the contemplation of this invention, namely, corn starch and aloe vera. Bar-Sholom uses neither of these agents.

Also, testing of the instant invention indicates that it is not effective in the treatment of acne.

In addition to the treatment of pseudofolliculitis barbae, it is intended that the present invention will also provide a product and method which will provide relief from pain caused by skin burns of all types and, further, will provide relief of cold sores generated by herpes Type II virus. A yet further application of the present invention is in treatment of simple razor burn irritation caused, after shaving upon skin of all racial types.

SUMMARY OF THE INVENTION

The instant invention comprises a topical agent of lotion-like consistency comprising a group of two solids mixed with a group of two liquids and, more particularly, the group of solids consisting of ninety per cent by volume of acetylsalicylic acid and ten per cent by volume of corn starch, and said group of liquids consisting of a volume of isopropyl alcohol sufficient to thoroughly wet to the point of saturation the mixture of solids. To the alcohol-dampened acetylsalicylic acid and corn starch is added a volume of aloe vera equivalent to a total volume of said solids and said isopropyl alcohol.

It is an object of the present invention to provide a product and method for the treatment of pseudofolliculitis barbae.

It is another object of the invention to provide a topical agent for the treatment of pseudofolliculitis barbae which may be employed without the occurrence of skin irritation or other harmful side effects.

It is a further object of the present invention to provide a product that will be applied to the skin to sooth the effects associated with skin burns of all types including "razor burn" irritation.

It is a yet further object of the invention to provide a topical preparation for the treatment of cold sores generated by the herpes Type II virus.

It is a further object of the present invention to provide a generalized anti-inflammatory topical preparation. The above and yet other objects and advantages of the present invention will become apparent in the hereinafter set forth Detailed Description of the invention and Claims appended herewith.

DETAILED DESCRIPTION OF THE INVENTION

The inventive topical preparation and method result from the combination of four ingredients, as follows:

Two types of solids are employed which, more particularly, comprise acetylsalicylic acid and corn starch. These solids are mixed accordingly to volume, and, more particularly, are mixed in the proportion of ninety percent by volume of acetylsalicylic acid to ten percent by volume of corn starch.

After the solids have been combined and completely mixed, there is added thereto a quantity of an alcohol, such as isopropyl alcohol. Sufficient volume is used to generously soak the mixed solids therewith.

After the above step, there is added a volume of aloe vera which is about equal in volume to the total volume resultant from the preceding two steps.

The above combination of components, when expressed as percentages by weight, are related approximately as follows:

| | |
|---|---|
| acetylsalicylic acid | 30 percent |
| corn starch | 3.5 percent |
| isopropyl alcohol | 16.5 percent |
| aloe vera | 50 percent |

The aloe vera should be used in the form of a gel and which is as pure as possible, e.g., at least ninety nine percent pure to thereby provide to the product a lotion-like consistency. As can be best determined, the above components are immiscible and act individually, in chemically unaltered states. The function of the individual components are as follows:

The acetylsalicylic acid acts as an anti-inflammatory which induces the mechanical relaxation of the curled beard hairs thereby eliminating the basic cause of pseudofolliculitis barbae. It has been found that acetylsalicylic acid, when used with the above described isopropyl alcohol and aloe, will eliminate the condition; however, the onset of the action will be delayed for thirty to forty minutes. The desired action of the acetylsalicylic acid, once initiated, will afford approximately eight to nine hours of relief from the condition, thus giving the product a suitable duration.

The corn starch operates to accelerate the onset of the action of the product. That is, with the inclusion of the corn starch as a part of the inventive formulation, the "razor bumps" start to shrink immediately and are practically non-existent within five minutes. It has been found that the corn starch, when used with the isopropyl alcohol and aloe vera as set forth herein, will demonstrate the same rapid onset of effectiveness and resolution of the condition. However, the duration of the product, without the acetylsalicylic acid, will be only in the range of two to three hours, after which point the condition will re-appear. When the starch is used with the acetylsalicylic acid, the said two solids will yield relief from the pseudofolliculitis condition within minutes and such relief will continue for a period of about to ten hours.

The use of alcohol serves as a carrier vehicle for the solids and, further, serves as an agent which dissolves oils and grease in the skin to thusly permit intimate contact of the said solid components with the skin, hair and hair follicles. Absent of the use of alcohol, the oily and fatty substances within the skin and facial hair will coat the solids rendering them substantially ineffective. Accordingly, the use of alcohol and, in particular, isopropyl alcohol, may be seen as an effective carrier agent for the active components of the acetylsalicylic acid and corn starch.

The aloe vera gel operates to establish the consistency and solid state texture of the resultant product. More particularly, the aloe vera is a non-oil based organic derivative selected to preclude coating of the said solid component particles with any material which would render them ineffective. Accordingly, aloe represents a consistency-providing agent which is not oil or fat based and which will not block the effectiveness of the solids or of the isopropyl alcohol in its function as a carrier.

The resultant lotion-like product which is provided by the aloe vera gel effects an even application of the lotion-like product on the skin while allowing the other three ingredients to operate effectively with respect to the skin, hair and hair follicles. Aloe vera is also noted for its soothing and anti-inflammatory properties i.e., its use as a sunburn medicament is well known.

The mechanical form of the topical agent may, through the use of well-known chemical expedients, become any of the group consisting of gel, soap, shaving foam, solution, cream ointment, lotion and stick.

The directions for the use of the product are as follows:
1. Wash the beard area with cold or lukewarm soapy water to remove oil and dirt particles from the skin.
2. Shave using whatever method is preferred.
3. Rinse the beard area with cold tap water to remove the debris of shaving, and then towel dry the beard area.
4. Apply the lotion of the inventive formulation to the beard area with the finger tips, applying a thin coat thereto.
5. Allow three to five minutes to dry.
6. Using a moist face cloth, gently wipe-off the excess lotion so that only the thinnest possible coating remains.
7. Allow several minutes to dry.
8. Use a preferred after-shave product to render the residual coating of lotion of the product nearly invisible.
9. Use daily as above.
10. Apply as an overnight cream in severe cases, in addition to the above set forth steps.

The inventive formulation has been tested on a limited basis, consisting of less that ten people, by Bioline Pharmaceuticals, in Fort Lauderdale, Florida. The results of this testing have been most positive.

It has also found that the inventive product and method will sooth pain from skin burns of all types. For example, conventional razor burns, sun burn, and other burn-like irritations of the skin.

Further, cold sores generated by herpes Type II virus have been helped by the application of the formulation described above. Limited trials of the product involving less that ten people have demonstrated that cold sores of this type can be relieved to a major degree through several usages of use of the product described herein.

Accordingly, while there has been shown and described the preferred embodiment of the present invention, it is to be appreciated that the invention may be embodied otherwise than is herein specifically shown and described, and that within said embodiment, certain changes may be made in the detail thereof without departing from the underlying principles of this invention within the scope of the Claims appended herewith.

Having thus described our invention, what we claim as new, useful and non-obvious and, accordingly, secure by Letters Patent of the United States is:

1. A topical agent consisting essentially of:
   (a) about ninety percent by volume of solid acetylsalicylic acid;
   (b) about ten percent by volume of solid corn starch, said volume of corn starch combined and thoroughly mixed with said acetylsalicylic acid;
   (c) a volume of alcohol sufficient to saturate said mixture of acetylsalicylic acid and corn starch with said alcohol; and
   (d) a non-oil based consistency providing agent, said agent comprising aloe vera, said agent having a volume of about equal to the combined volume of said acetylsalicylic acid, corn starch and alcohol, said agent mixed therethrough.

2. A process for producing a composition for treatment of pseudofolliculitis barbae comprising:
   (a) mixing about 90 percent by volume of solid acetylsalicylic acid with about 10 percent by volume of solid corn starch, said volume of corn starch combined and thoroughly mixed with said acetylsalicylic acid;
   (b) adding isopropyl alcohol to the above in a volume sufficient to saturate said mixture of acetylsalicylic acid and corn starch with said alcohol; and
   (c) blending aloe vera gel with the mixture of Steps (a) and (b) above, using a volume of aloe gel about equal to the combined volume of the mixture of Steps (a) and (b) above.

3. The agent as recited in claim 1 in which said aloe vera comprises aloe vera gel that is at least ninety nine percent pure.

4. The agent as recited in claim 1 in which said alcohol comprises isopropyl alcohol.

5. A method for treating pseudofolliculitis barbae which comprises applying to the affected area of the skin an effective amount of the agent according to claim 1 for providing topical relief from irritation due to pseudofolliculitis barbae.

6. The method according to claim 5 in which the active elements thereof comprise components of a cosmetically acceptable topical preparation selected from the group consisting of gel, soap, shaving foam, solution, cream, ointment, lotion and stick.

7. A composition for topical treatment of pseudofolliculitis barbae, consisting essentially of:

| acetylsalicylic acid | 30 percent |
| --- | --- |
| corn starch | 3.5 percent |
| isopropyl alcohol | 16.5 percent and |
| aloe vera | 50 percent |

8. The composition of claim 7 in which the aloe is a gel.

9. The composition of claim 8 in which the aloe is at least 99% pure.

10. A method for treating pseudofolliculitis barbae comprising applying an effective amount of the composition of claim 7 to the face for providing topical relief from irritation due to pseudofolliculitis barbae.

11. A method for treating pseudofolliculitis barbae comprising applying an effective amount of the composition of claim 9 to the face for providing topical relief from irritation due to pseudofolliculitis barbae.

12. A topical agent for the treatment of psuedofolliculitis barbae comprising the product of the process of claim 2.

* * * * *